(12) United States Patent
Smith et al.

(10) Patent No.: US 8,494,636 B2
(45) Date of Patent: Jul. 23, 2013

(54) FEED-THROUGH CONNECTOR ASSEMBLY FOR IMPLANTABLE PULSE GENERATOR AND METHOD OF USE

(71) Applicants: Alexander K. Smith, Chesterland, OH (US); Daniel N. Kelsch, Fairview Park, OH (US); Carlos A. Navarro, Buffalo, NY (US)

(72) Inventors: Alexander K. Smith, Chesterland, OH (US); Daniel N. Kelsch, Fairview Park, OH (US); Carlos A. Navarro, Buffalo, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/721,348

(22) Filed: Dec. 20, 2012

(65) Prior Publication Data

US 2013/0110209 A1    May 2, 2013

Related U.S. Application Data

(63) Continuation of application No. 13/074,358, filed on Mar. 29, 2011, now Pat. No. 8,369,951.

(51) Int. Cl.
*A61N 1/00* (2006.01)
(52) U.S. Cl.
USPC .......................................................... 607/37
(58) Field of Classification Search
USPC .......................................................... 607/37
See application file for complete search history.

(56) References Cited

U.S. PATENT DOCUMENTS

| | | | |
|---|---|---|---|
| 4,469,104 | A | 9/1984 | Peers-Trevarton |
| 4,995,389 | A | 2/1991 | Harris |
| 5,795,165 | A | 8/1998 | Jarl |
| 5,899,930 | A | 5/1999 | Flynn et al. |
| 6,498,952 | B2 | 12/2002 | Imani et al. |
| 6,654,641 | B1 | 11/2003 | Froberg |
| 6,662,035 | B2 | 12/2003 | Sochor |
| 6,749,358 | B2 | 6/2004 | Balsells |
| 6,878,013 | B1 | 4/2005 | Behan |
| 6,895,276 | B2 | 5/2005 | Kast et al. |
| 6,895,876 | B2 | 5/2005 | Bergere et al. |
| 7,070,455 | B2 | 7/2006 | Balsells |
| 7,274,963 | B2 | 9/2007 | Spadgenske |
| 7,537,474 | B2 | 5/2009 | Deininger et al. |
| 7,654,843 | B2 | 2/2010 | Olson et al. |
| 7,690,953 | B2 | 4/2010 | Boyd et al. |
| 7,711,427 | B2 | 5/2010 | Janzig et al. |

(Continued)

FOREIGN PATENT DOCUMENTS

| | | |
|---|---|---|
| DE | 19917779 | 11/2000 |
| EP | 1062986 | 12/2000 |

(Continued)

OTHER PUBLICATIONS

European Search Report; Application No. EP 12 16 3521; Reference: PT02407EP; Application: Greatbatch Ltd.; Place of Search: Munich; Date of Completion of Search: Sep. 19, 2012.

(Continued)

*Primary Examiner* — George Manuel
(74) *Attorney, Agent, or Firm* — Pearne & Gordon LLP

(57) ABSTRACT

A connector assembly for a medical device for connecting the medical device to a relatively large plurality of electrodes that can support, in some cases, 24 or more stimulation channels for stimulating one or more stimulation regions of a patient. Also the medical device and the stimulation system and the stimulation therapy utilizing the connector assembly.

29 Claims, 11 Drawing Sheets

U.S. PATENT DOCUMENTS

| | | |
|---|---|---|
| 7,890,175 B1 | 2/2011 | Rey et al. |
| 2003/0040780 A1 | 2/2003 | Haeg et al. |
| 2003/0179536 A1 | 9/2003 | Stevenson et al. |
| 2004/0167582 A1 | 8/2004 | Tvaska et al. |
| 2006/0004419 A1 | 1/2006 | Olbertz |
| 2006/0047322 A1 | 3/2006 | Naviaux |
| 2007/0202728 A1 | 8/2007 | Olson et al. |
| 2008/0071320 A1 | 3/2008 | Brase |
| 2008/0246231 A1 | 10/2008 | Sjostedt et al. |
| 2008/0255631 A1 | 10/2008 | Sjostedt et al. |
| 2009/0017668 A1 | 1/2009 | Deininger et al. |
| 2009/0099620 A1 | 4/2009 | Rebentisch |
| 2009/0118778 A1 | 5/2009 | Biggs, Jr. et al. |
| 2009/0243756 A1 | 10/2009 | Stevenson et al. |
| 2009/0258519 A1 | 10/2009 | Dilmaghanian et al. |
| 2009/0312835 A1 | 12/2009 | Stevenson |
| 2010/0016928 A1 | 1/2010 | Zdeblick et al. |
| 2010/0109966 A1 | 5/2010 | Mateychuk et al. |
| 2010/0191299 A1 | 7/2010 | Ayzenberg |
| 2010/0274309 A1 | 10/2010 | Knipfer et al. |
| 2011/0029036 A1 | 2/2011 | Yamamoto et al. |
| 2011/0137414 A1 | 6/2011 | Litzke et al. |
| 2011/0184479 A1 | 7/2011 | Kast et al. |
| 2011/0282410 A1* | 11/2011 | Lim ................................ 607/36 |
| 2012/0253424 A1 | 10/2012 | Smith et al. |

FOREIGN PATENT DOCUMENTS

| | | |
|---|---|---|
| JP | 54057101 | 5/1979 |
| JP | 10223346 | 8/1998 |
| WO | 0064535 | 11/2000 |
| WO | 2005014108 | 2/2005 |
| WO | 2005105207 | 11/2005 |
| WO | 2011011223 | 1/2011 |
| WO | WO2011011223 A1 | 1/2011 |
| WO | 2011017432 | 2/2011 |

OTHER PUBLICATIONS

CPA Global in Alexandria, VA; Patentability Search for Feed Through Connection; Requested by: Tom Woods; Date of Letter: Dec. 5, 2012; CPA Global Ref. No. P201100193; Date of Report: Mar. 1, 2011.

European Search Report; Date of Report: Apr. 17, 2013; Reference: PT02775EP; Applicant: Greatbatch Ltd.; Application No. EP 13151690.8-1652; Place of Search: Munich; Date of Completion of Search: Apr. 11, 2013.

* cited by examiner

FEED-THROUGH CONNECTOR ASSEMBLY FOR IMPLANTABLE PULSE GENERATOR AND METHOD OF USE

CROSS-REFERENCES TO RELATED APPLICATIONS

This application is a continuation of U.S. patent application Ser. No. 13/074,358, filed on Mar. 29, 2011, and incorporated herein by reference.

BACKGROUND OF THE INVENTION

This application relates generally to a connector for a medical device and, more specifically, to a feed-through connector assembly for connecting to a connector assembly for achieving electrical contact with an Internal Pulse Generator. Medical devices have been implanted in patients to perform a variety of tasks. For example, programmable pulse generating systems are used to treat chronic pain by providing electrical stimulation pulses from an epidural electrode array placed near a patient's spine. Such Spinal Cord Stimulation (SCS) is useful for reducing pain in certain populations of patients. SCS systems typically include one or more electrodes connected to one or more connectors of an External Pulse Generator (EPG) or an Implanted Pulse Generator (IPG) via leads. In the case of an EPG, the lead must be connected to the EPG via an exit from the body. The pulse generator, whether internal or external, generates pulses that are typically delivered to the dorsal column fibers within the spinal cord through the electrodes which are implanted along or near the dura of the spinal cord. In a typical situation, the attached leads exit the spinal cord and are tunneled around the torso of the patient to a subcutaneous pocket where the IPG is implanted, or the wires exit the patient for connection to the EPG.

U.S. Pat. Nos. 7,537,474 and 6,895,876, incorporated herein by reference, disclose a connector solution for an implantable pulse generator (IPG) utilizing a coiled spring inside a contact block. The ends of the spring are welded together yielding a torus shape through which the in-line lead is inserted. The spring coils cant to conform to the contact ring of an IPG lead, thus making electrical contact. Each coil which contacts both the lead and the block forms a separate redundant electrical contact.

However, current connectors that could be used for connecting the IPG contacts to a connector assembly as disclosed herein have a number of shortcomings. First, support for IPGs with up to, or more than, 24-26 contacts has not been supported. Furthermore, previous connectors typically used hand routed feed through (FT) wires to connect directly to the lead connection stack so no FT connection was required when lead frame designs were employed (e.g. MDT Restore) the FT pitch was approximately 50% larger (~0.075") and no stress relief was required due to a much larger available weld area than would be desirable. Furthermore, it would be useful to provide IPG devices with multiple lead ports that have contact stacks that are assembled as a single unit, and tested in a single fixture before final assembly of the IPG, to determine that all channels have electrical continuity to inserted electrode pin (s) that represents a connection end of a stimulation lead.

SUMMARY OF THE INVENTION

Provided are a plurality of embodiments the invention, including, but not limited to, a connector assembly for installing in an IPG device including a plurality of conducting IPG pins, the connector assembly for connecting the IPG device to a contact assembly including a plurality of contact blocks, the connector assembly comprising a plurality of conducting leads, each one of the conducting leads including: a contact block connector at one end of the lead adapted for connecting to a corresponding one of the contact blocks of the contact assembly, the contact block connector including a contact portion adapted for electrically contacting a contact portion of the corresponding contact block; an IPG connector at another end of the lead for electrically connecting to the IPG device, the IPG connector including a flat terminal portion and a curved portion split to receive a corresponding one of the conductive IPG pins of the IPG such that the flat terminal portion is adapted to be received against a head provided at the end of the corresponding IPG pin and wherein the split portion is adapted to receive a body of the corresponding IPG pin; and a conductive wire portion connecting the contact block connector to the IPG connector, wherein the conductive wire portion is adapted to be routed through various structures of the contact assembly.

Also provided is a connector assembly for installing in an IPG device including a plurality of conducting IPG pins, the connector assembly for connecting the IPG device to a contact assembly, the connector assembly comprising: a plurality of conducting leads, each one of the conducting leads including: a contact assembly connector at one end of the lead adapted for connecting to a corresponding contact on the contact assembly, an IPG connector at another end of the lead for electrically connecting to the IPG device, the IPG connector including a flat terminal and a curved portion split to receive a corresponding one of the conductive IPG pins such that the flat terminal is adapted to be received against a head provided at the end of the corresponding IPG pin, and a conductive wire portion connecting the contact block connector to the IPG connector, wherein the conductive wire portion is adapted to be routed through various structures of the contact assembly; and a first installation part connected to a plurality of the conductive leads for holding the plurality of conductive leads together.

Also provided is a connector assembly for installing in an IPG device including a plurality of conducting pins, the connector assembly for connecting the IPG device to a contact assembly including a plurality of contact blocks, the connector assembly comprising: a plurality of conducting leads, each one of the conducting leads including: a contact block connector at one end of the lead adapted for connecting to a corresponding one of the contact blocks of the contact assembly, the contact block connector including a portion adapted for electrically contacting a portion of the corresponding contact block, an IPG connector at another end of the lead for electrically connecting to the IPG device, the IPG connector including a flat terminal and a curved portion split to receive a corresponding one of the conductive pins of the IPG such that the flat terminal is adapted to be received against a head provided at the end of the corresponding pin, and a conductive wire portion connecting the contact block connector to the IPG connector, wherein the conductive wire portion is adapted to be routed through various structures of the contact assembly by bends provided in the wire portion; a first installation part connected to a plurality of the conductive leads by connecting, via a removable connection, to the contact block connector of the plurality of conductive leads; and a second installation part connected to a plurality of the conductive leads by connecting, via a removable connection, to the IPG connector of the plurality of conductive leads, wherein the first installation part and the second installation part are adapted to be removed when the connector assembly is installed in the IPG.

Also provided is a connector assembly for installing in an IPG device including a plurality of conducting IPG pins, the connector assembly for connecting the IPG device to a contact assembly including a plurality of contact blocks, the connector assembly comprising a plurality of conducting leads, each one of the conducting leads including: a contact block connector at one end of the lead adapted for connecting to a corresponding one of the contact blocks of the contact assembly, the contact block connector including a flat portion adapted for electrically contacting a flat portion of the corresponding contact block; an IPG connector at another end of the lead for electrically connecting to the IPG device, the IPG connector including a flat terminal and a curved portion split to receive a corresponding one of the conductive IPG pins of the IPG such that the flat terminal is adapted to be received against a head provided at the end of the corresponding IPG pin, wherein the IPG connector further comprises a flat portion between the curved portion and the conductive wire portion, the flat portion being adapted for being placed against a corresponding portion of the IPG, wherein the IPG connector is adapted such that the curved portion is in compression when the IPG connector is installed in the IPG, the compression for keeping the flat terminal pressed against the head of the IPG pin of the IPG; and a conductive wire portion connecting the contact block connector to the IPG connector, wherein the conductive wire portion is adapted to be routed through various structures of the contact assembly by bends provided in the wire portion.

Still further provided is an IPG for stimulating a stimulation region of a patient comprising an IPG including a contact assembly connected to the IPG using a connector assembly such as one described above.

Further provided are a system and a method of therapy, such as one using the above IPG, for example.

Also provided are additional embodiments of the invention, some, but not all of which, are described hereinbelow in more detail.

BRIEF DESCRIPTION OF THE DRAWINGS

The features and advantages of the examples of the present invention described herein will become apparent to those skilled in the art to which the present invention relates upon reading the following description, with reference to the accompanying drawings, in which.

DETAILED DESCRIPTION OF THE EXAMPLE EMBODIMENTS

Provided is a design for a welded feed through (FT) connector and its method of assembly and use that allows repeated flexing between a header and a hermetic enclosure of an active implantable medical device (e.g., an IPG) and minimizes stress to the electrical connection between the FT wire and the "lead frame" that leads to the contact stack for a stimulation lead. This is particularly important for welds made between dissimilar materials (e.g., Pt to MP35N or SS 316LVM) as these tend to have poorer mechanical attachment than those of similar materials (e.g., Pt to Pt).

The feed-through connection scheme described herein facilitates ease of assembly and long-term durability of a complete insert molded header to a hermetic enclosure containing an electronic stimulation circuit. The FT connector is especially designed for applications using laser welding of dissimilar materials such as platinum (Pt) IPG pins to MP35N or SS 316 LVM lead frame, but might also be useful for either similar material (e.g., Pt pins to Pt lead frame) or possibly resistance welding processes instead of laser welding.

Figure 1:
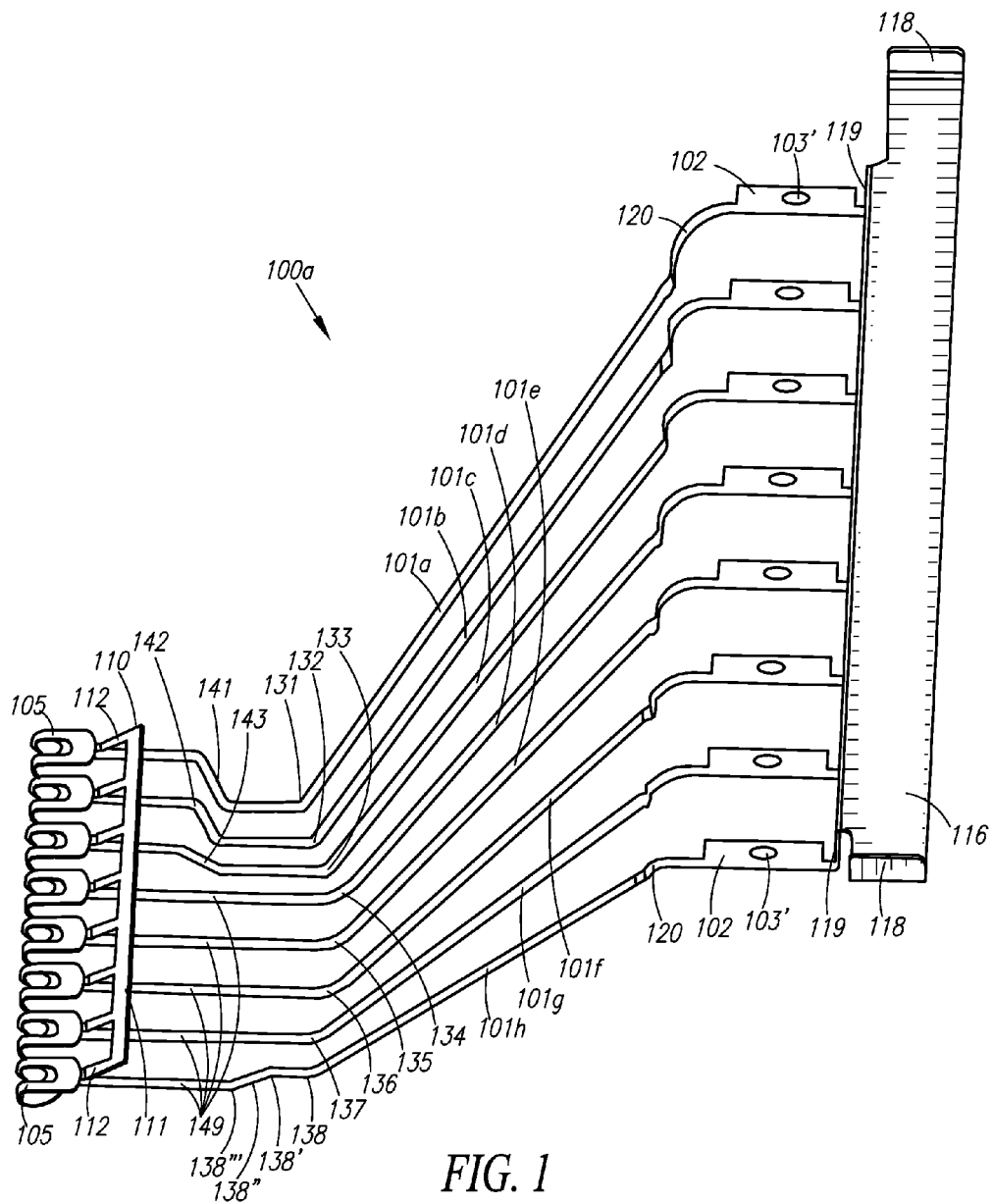
FIG. 1 shows an example embodiment of a first arrangement of a lead frame for use with an example IPG.
Figure 2:
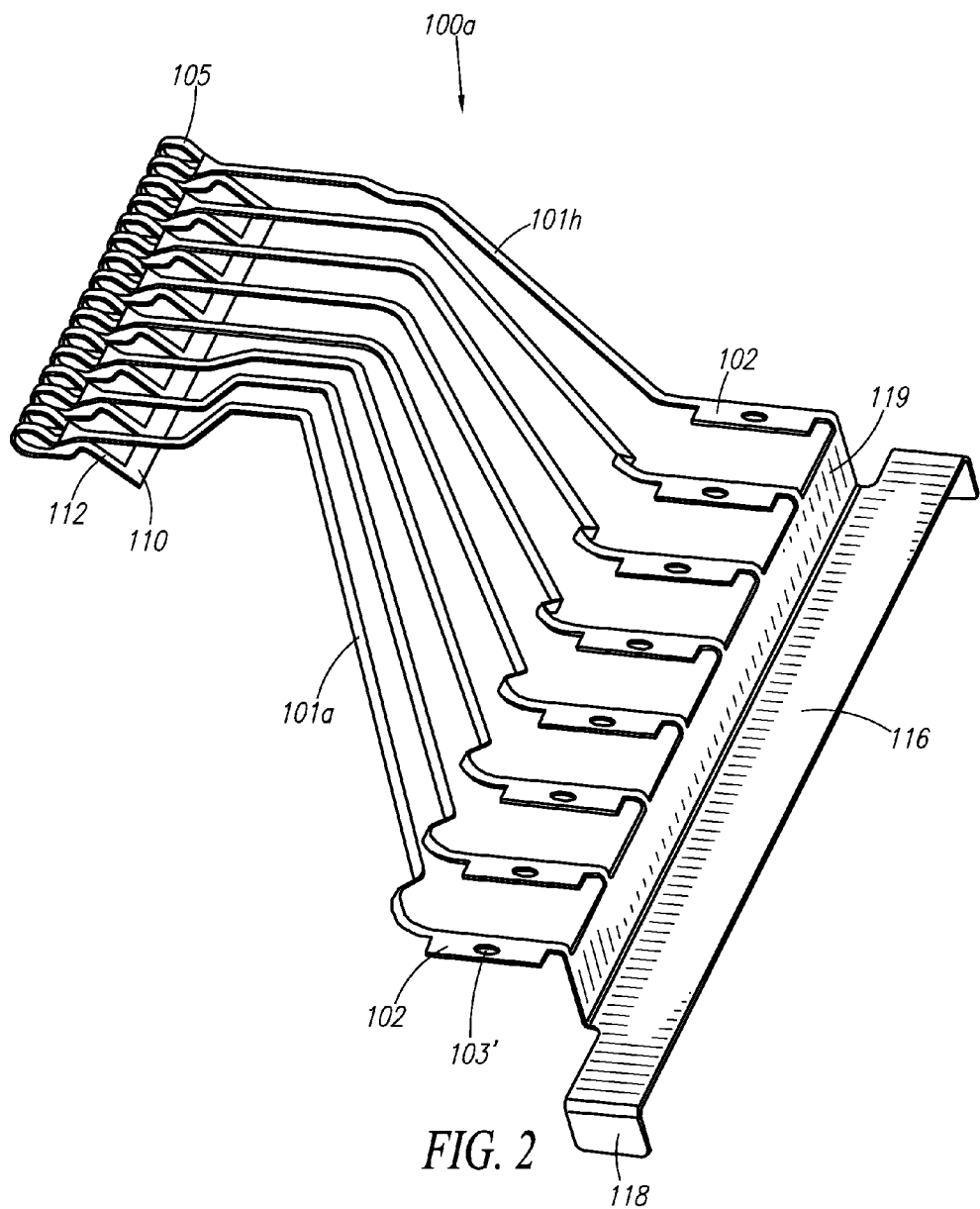
FIG. 2 shows another view of the lead frame of FIG. 1.

FIGS. 1 and 2 show different views of an example embodiment of a feed-through connector that can be used. The connector is arranged in a lead frame 100 after manufacture but before final use by connecting a plurality of leads 100 together by using a first temporary connecting structure 116 at one end of the lead frame 100 connected to the connector assembly connector lead end (CA lead end) 102 of each of the leads 101 at 119, and a second temporary connecting structure 110 connected to the IPG connector end (IPG end) 105 of each of the leads 101 at 112. Alternatively, as shown in FIG. 8 for a testing lead frame 100', the leads 101 can be connected together by using a web, such as an insulating web. The web structure in FIG. 8 is an embodiment used for testing and proof of concept, whereas the actual product would utilize the structure like that shown in FIGS. 1-2 and 7.

Figure 5:
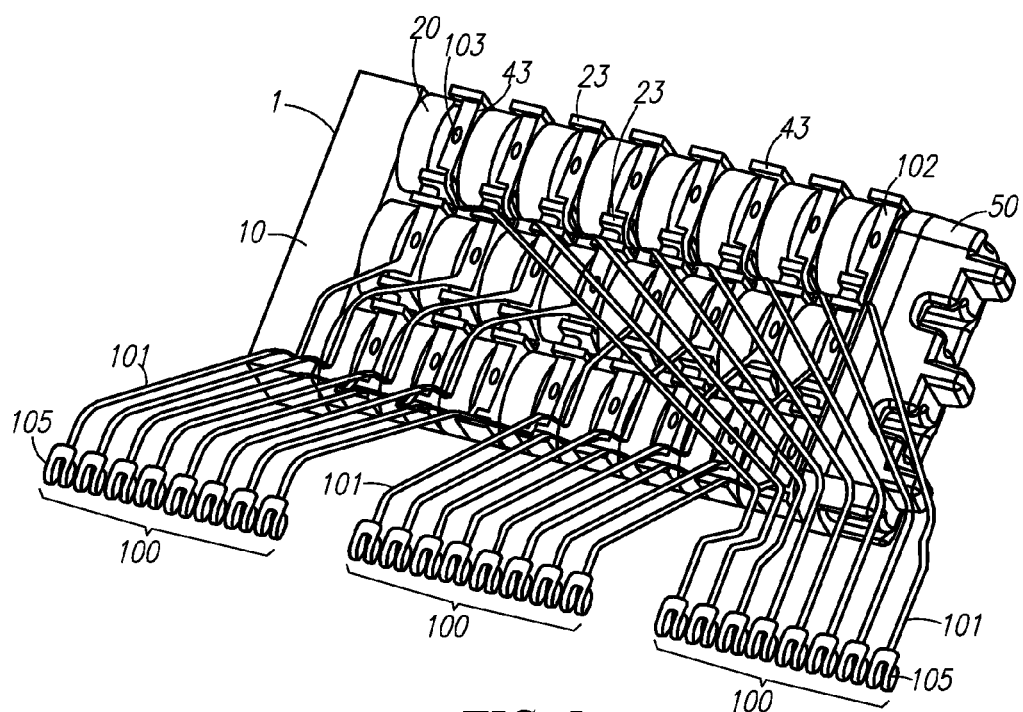
FIG. 5 shows the example contact assembly of FIG. 3 with connecting leads of three example arrangements of lead frames installed.

After installation, the temporary structures 116 and 110 can be removed, such as by breaking them off manually, for example. These structures would be made of the same materials as the lead frame itself, i.e., MP35N, Pt—Ir, or Stainless Steel, for example. The lead frame 100 has a plurality of leads 101 grouped together (as described above), such as into groups of 8 in the example embodiment. Typically, each lead frame 100 is formed into a shape to fit the contours of the IPG in which it will be installed. As shown in FIG. 5, each one of the three lead frames 100a, 100b, and 100c are formed with different routings and bendings of the leads 101 for connecting to a connector assembly 1.

For example, in the example embodiment of FIGS. 1 and 2, the leads 101 of lead frame 100 are formed into a particular shape for fitting as the rightmost lead frame 100a of FIG. 5. Each lead 101 (101a-101h) has a CA lead end 102 formed into a wider portion (tab) with a weld hole 103', the end 102 for connecting to a contact surface of a connector assembly by welding at weld hole 103' (described below). The CA lead ends 102 are all provided in a common plane for connecting to the connector assembly 1

The leads 101 are made narrower after the CA ends 102, and have a curved portion 120 formed to route the leads to fit the IPG assembly. A relatively long run in the leads 101 is provided until a second curved portion 131-138 is provided in corresponding leads 101, shown as 101a to 101h. As shown, each of the curved portions 131-138 of the eight shown leads 101a-101h has a different curvature, with the curve being much sharper the 131 on lead 101a and gradually being less sharp (i.e., having a larger radius of curvature) in consecutive curves 132-136 (leads 101b-101g), with lead 101g at 137 beginning to get sharper, and lead 101h actually has a first curve 138, a plateau portion 138' a second curve portion 138", and a third curve portion 138'".

After these curves leads 101d-101h have a relatively long flat portion 149, while three of the leads 101a-101c have additional curved portions to step the leads up. Finally, the IPG ends 105 on each of the leads 101 are provided in a common plane, each for connecting to the IPG connector pins 160 of the IPG 61, as shown in FIG. 7.

Figure 11:
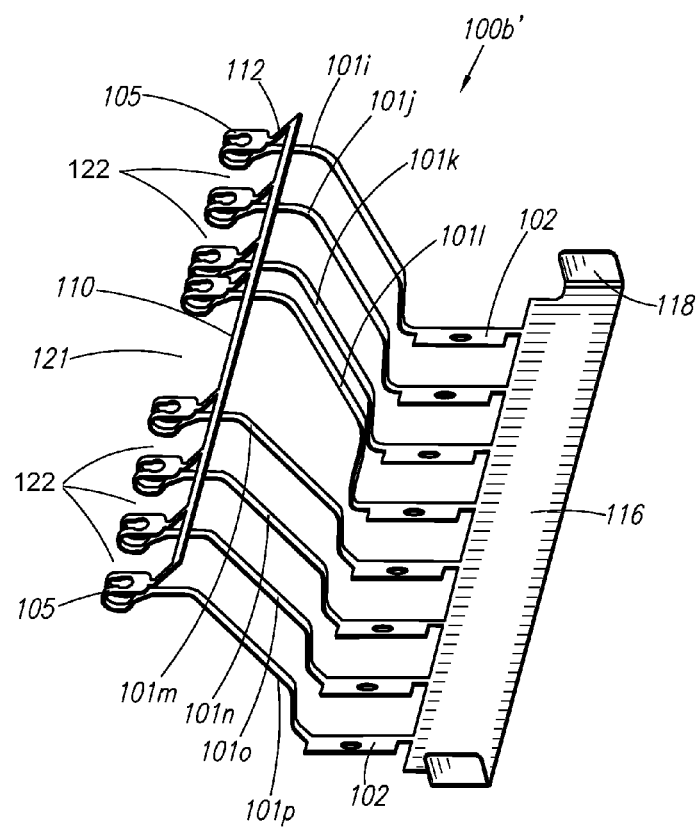
FIG. 11 shows the example embodiment of the second arrangement of a lead frame for use with the example IPG.
Figure 12:
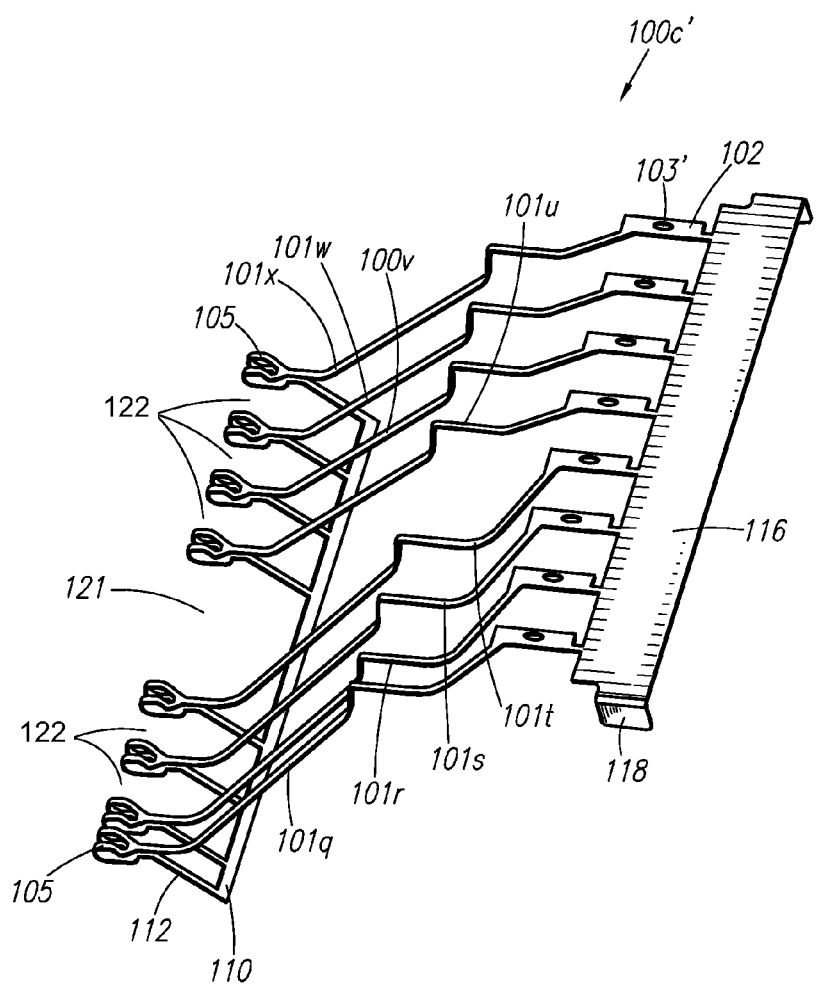
FIG. 12 shows the example embodiment of the third arrangement of a lead frame for use with the example IPG.
Figure 13:
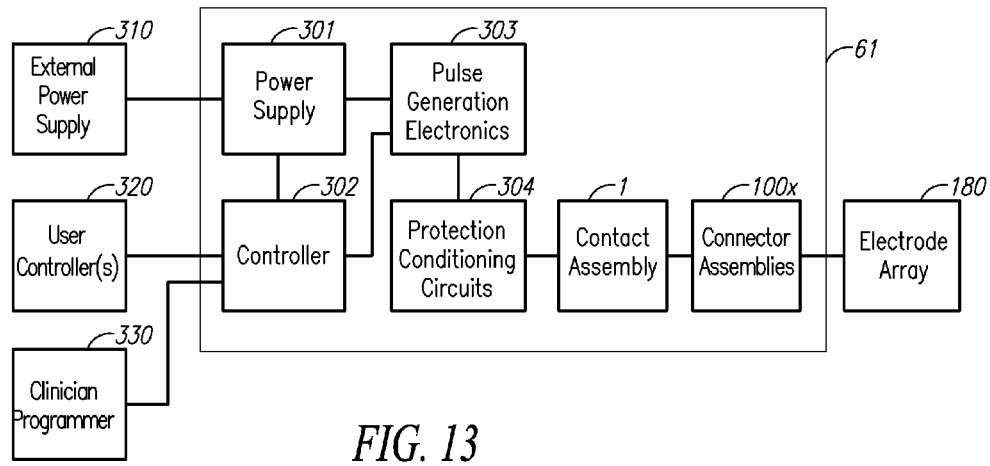
FIG. 13 is a block diagram showing example components of a pulse stimulation system using the example connector assembly including the example contact assembly and example lead frames.
Figure 14:
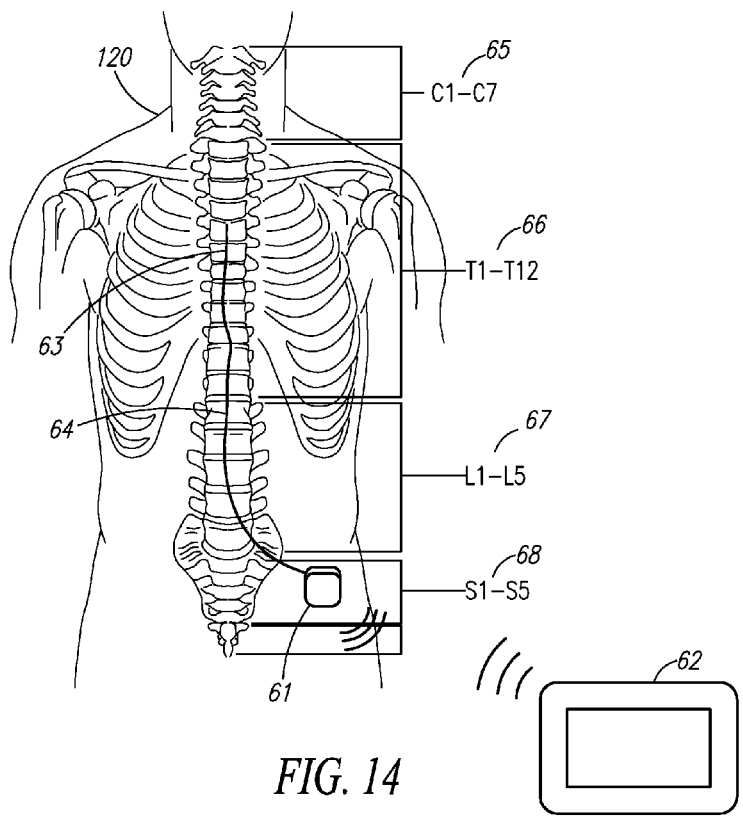
FIG. 14 is a diagram illustrating an example medical application of the pulse stimulation system of FIG. 13.

The other lead frames 100b' and 100c' are formed with leads routed differently in order to fit the contours within the IPG, as shown in FIGS. 11 and 12, as the specific routing is dependent on the design of the IPG and connector assembly, with the lead frame example routing described above merely being provided as an example to show the routing flexibility of the design. But as shown in FIG. 7, all of the IPG ends 105 are coplanar and the CA ends 102 are coplanar in the example implementation shown in that figure.

Figure 5A:
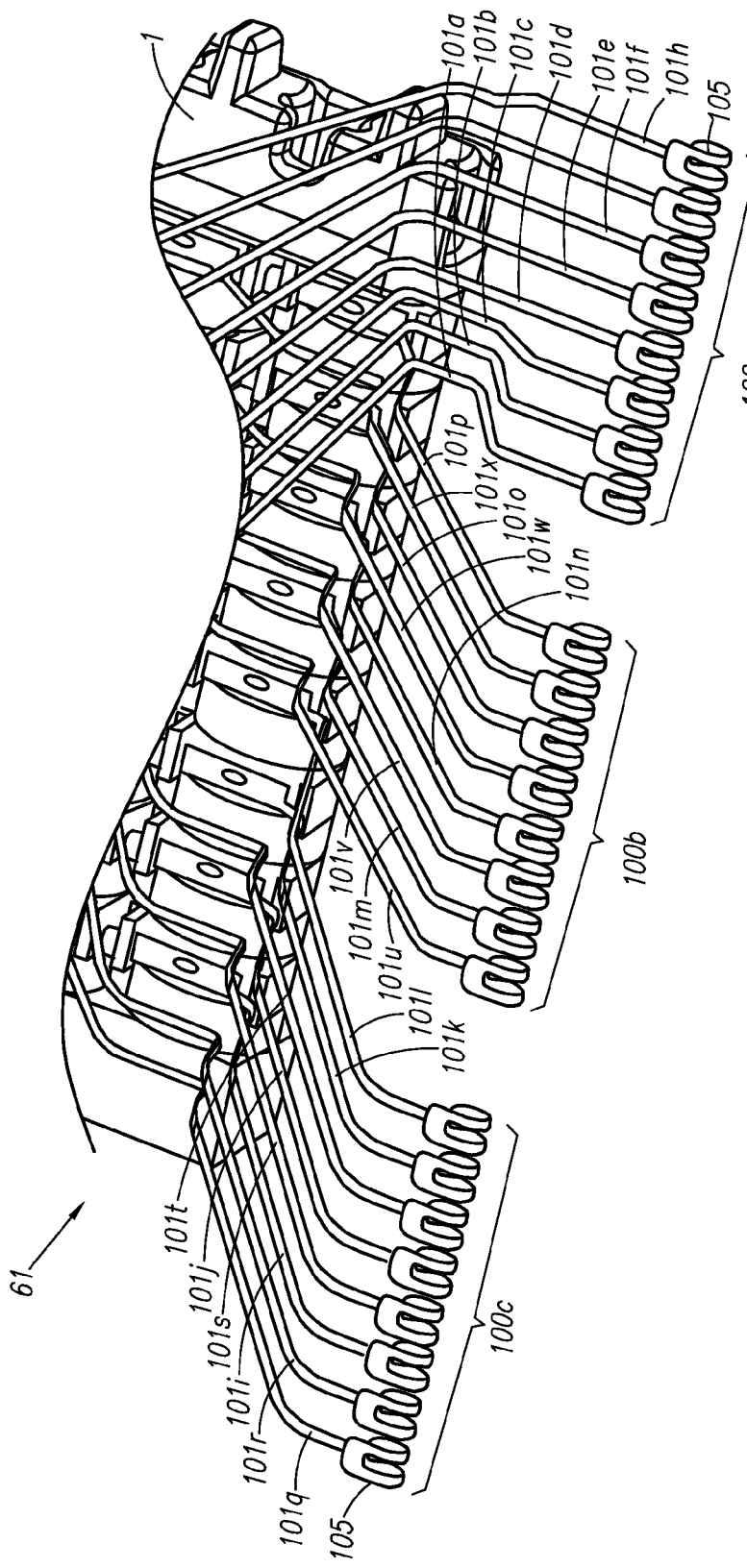
FIG. 5A shows a closeup of the example assembly of FIG. 5.

As shown in FIG. 5A, for the Example embodiment using the example IPG, the lead frames 100b' and 100c' of FIGS. 11 and 12 are installed in a manner that interleaves the leads 101i-101p of lead frame 100b' (FIG. 11) among some of the leads 101q-101x of lead frame 100c' (FIG. 12) into groupings 100b and 100c of FIG. 5A. Accordingly, the groupings 100b, 100c of the leads 101 shown in FIG. 5A do not correspond completely to the groupings of the individual leads of the lead frames 100b' and 100c' because of such interleaving, which "interleaves" some of the leads such that some of the leads of lead frame 100b' are provided in grouping 100c (i.e., leads 101i-101l) whereas some of the leads of lead frame 100c' are provided in grouping 100b (i.e., leads 101u-101x) in the manner illustrated in FIG. 5A. The gaps 122 between the leads of the lead frames 100b' and 100c' thus allow for such interleaving of the leads, while the larger gaps 121 show where the leads transition from one grouping 100b to the other grouping 100c.

Figure 7:
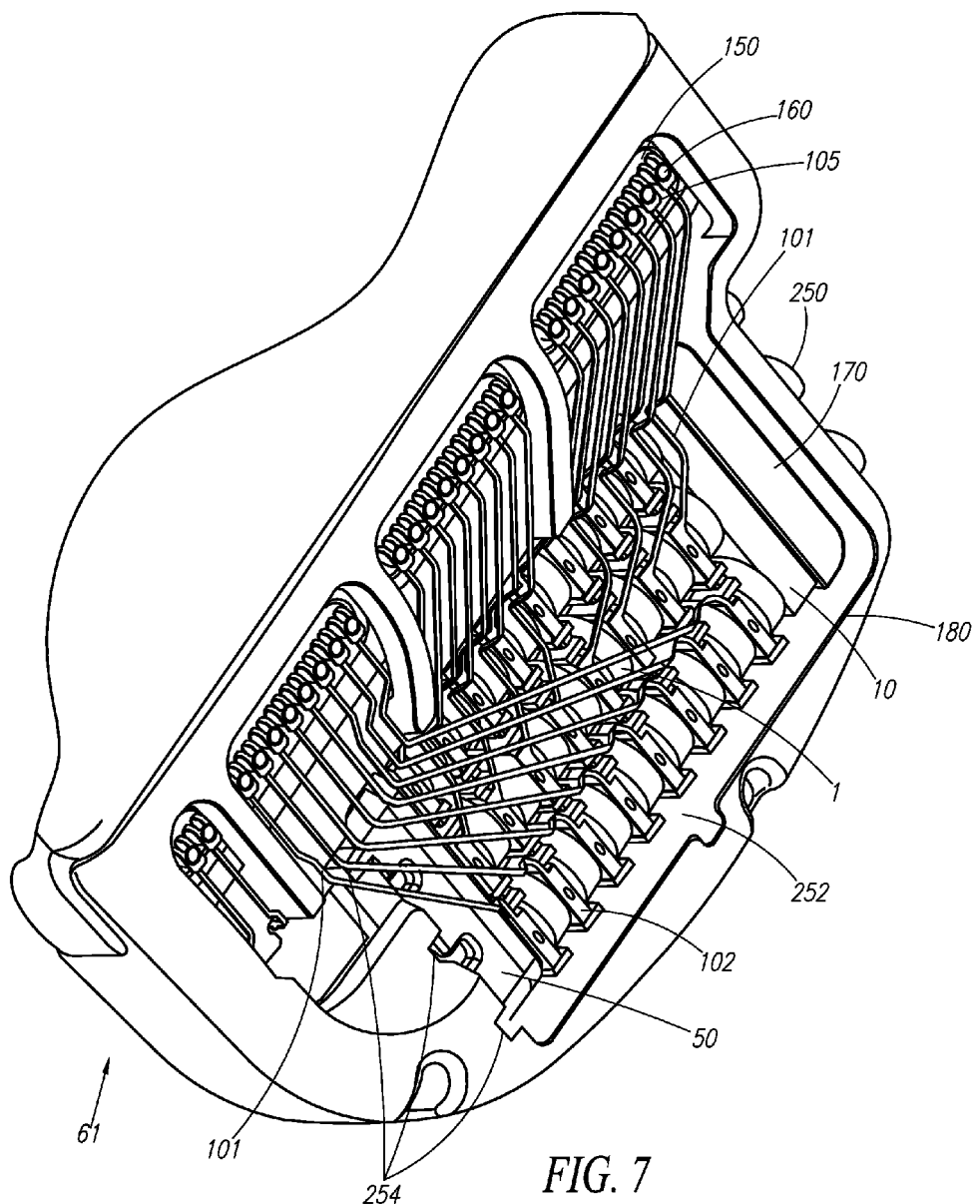
FIG. 7 shows the contact assembly of FIG. 3 connected to an IPG using three lead frames.
Figure 8:
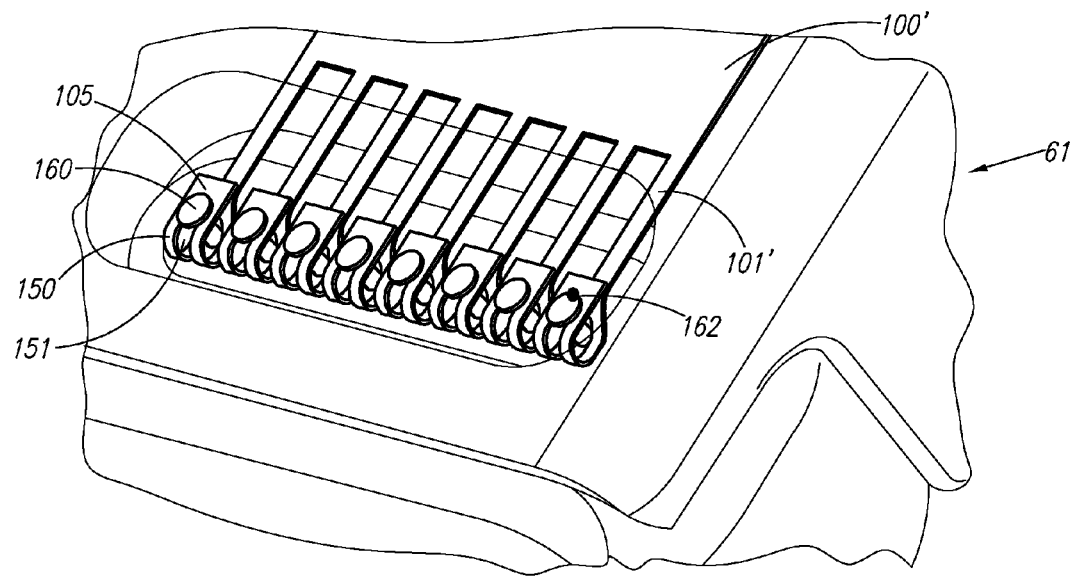
FIG. 8 shows a testing lead frame connected to the example IPG showing how the ends of leads of the lead frame may connect to corresponding IPG pins on the IPG.
Figure 9:
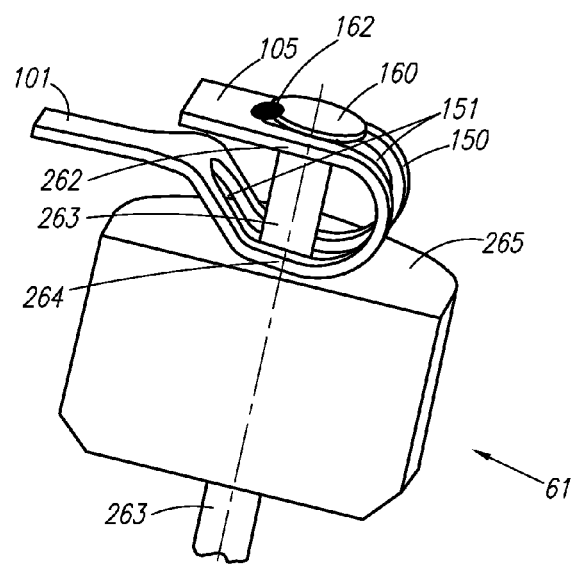
FIG. 9 shows a close up of how an example end of a lead of the example lead frame connects to an IPG pin of the example IPG.

FIG. 8 shows a testing lead frame 100' with IPG lead ends 150 connected to an IPG 61 in the manner of the lead frame 100 (shown in FIG. 7). As shown in FIG. 9, the overall geometry and especially the U-shaped portion 150 of the IPG lead end 105 are configured to flex when the header is incidentally bent relative to the hermetic electronics enclosure of the IPG. This protects the welded portion of the connection from stress so that the mechanical integrity of the electrical connection is maintained. This benefit was clearly shown by a finite element analysis study of the proposed designs.

The weld 162 used for welding the IPG end 105 of the lead 101 to the IPG pin head 160 may or may not be provided on each of the ends 105, as desired. The flexing of the end 105 (described in more detail below) may be sufficient to ensure electrical connectivity between the IPG pin 160 and the lead 101 without requiring welding all of the IPG ends 105, but it is preferable to provide a 162 on each end 105 in order to ensure proper electrical connections and physical stability. If desired, multiple welds could be used on each end 105 to increase the reliability of the connection. In particular, two welds per end, provided opposite each other on the end 105 but in contact with the pin head 160, would be useful for additional structural strength and electrical connectivity. Or one continuous weld over the pin head 160 could be utilized instead of multiple welds.

Further referring to FIG. 9, it is shown that the IPG ends 105 have a flat portion 262 at the end of one branch of the U-shaped portion 150 for being placed against and electrically contacting the IPG pin head 160, and a second flat portion 264 at the end of the other branch of the U-shaped potion 150 for being placed against the ceramic portion 265 of the IPG. These flat portions 262, 264, in combination with the U-shaped portion 150, cooperate to compress the flat portions 262, 264 against the respective head/ceramic surfaces to keep the IPG end in compression, and thus in place, and ensuring, in combination with the welds 162, good electrical connectivity between the leads 101 and their respective IPG pins 263. As shown, the split section 151 in the end 105 accepts the pin body portion of the pin 263.

Some of the advantages of these designs disclosed herein are:
1. Protects the welded joint 162 from stress due to flexing:
2. The assembly is self fixturing because of two features: Referring to FIGS. 7-9, the split section 151 in the U-shaped portion 150 of the IPG Lead ends 105 of the individual leads 101 of the lead frame 100/100' causes the individual connection features on the lead frame to self align with its respective IPG pin 263. When the U-shaped portion 150 of the IPG lead end 105 is dimensioned such that the parallel sides of the U are slightly more separated than the high dimensional limit of the space between the IPG ceramic portion 265 and the underside of the IPG pin head 160 the two elements are then positioned so as to provide intimate contact for the weld zone 162, a desirable condition for a successful weld.
3. The lead frame is further configured so that when the lead frame experiences distortion due to header bending, it remains clear of the FT flange 267 (see FIG. 10, which shows a partial view of an example arrangement of the IPG pins 263 on an IPG 61). This protects against the possibility of the leads 101 of the lead frame 100 making an electrical short to the FT flange 267.
4. The preceding benefits can all be accomplished at a compact spacing of 0.05" between the IPG pins 263, allowing for an IPG device with a higher number of contacts in a smaller overall device configuration that would otherwise be possible.

The lead frame can be utilized with a stack connector assembly that allows IPG devices with multiple lead ports to have contact stacks that are assembled as a single unit and tested in a single fixture before assembly to determine that all channels have electrical continuity to an inserted electrode pin that represents the connection end of a stimulation lead or plurality of such leads. FIG. 5 (described in more detail below) shows how the lead frame, with removable parts removed, would be connected to such a connector assembly 1.

Figure 3:
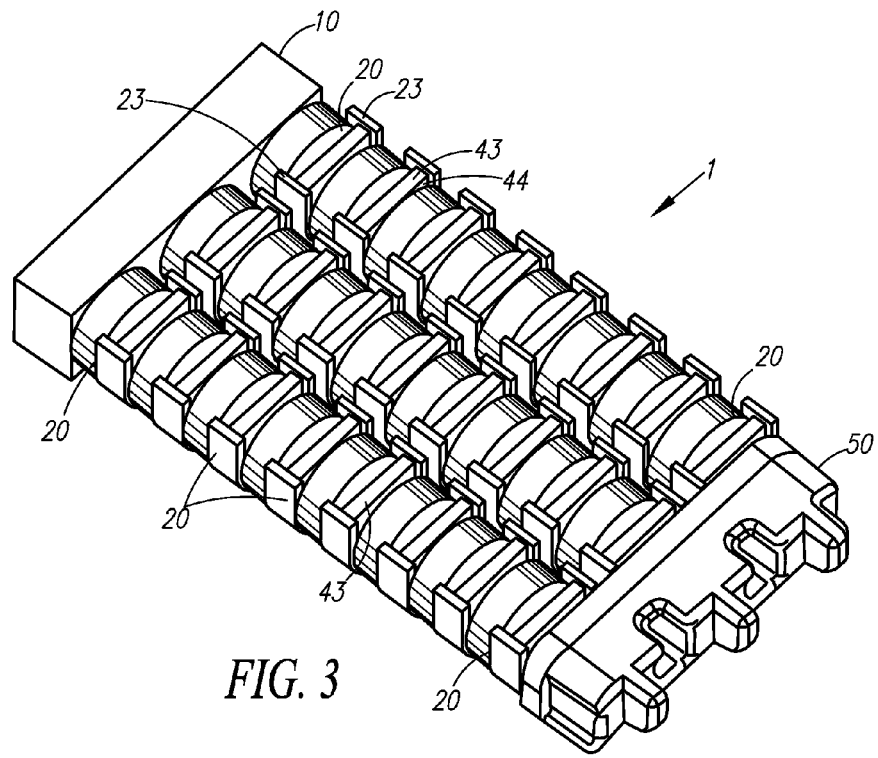
FIG. 3 shows an example embodiment of a contact assembly for use with the lead frame of FIG. 1.
Figure 4:
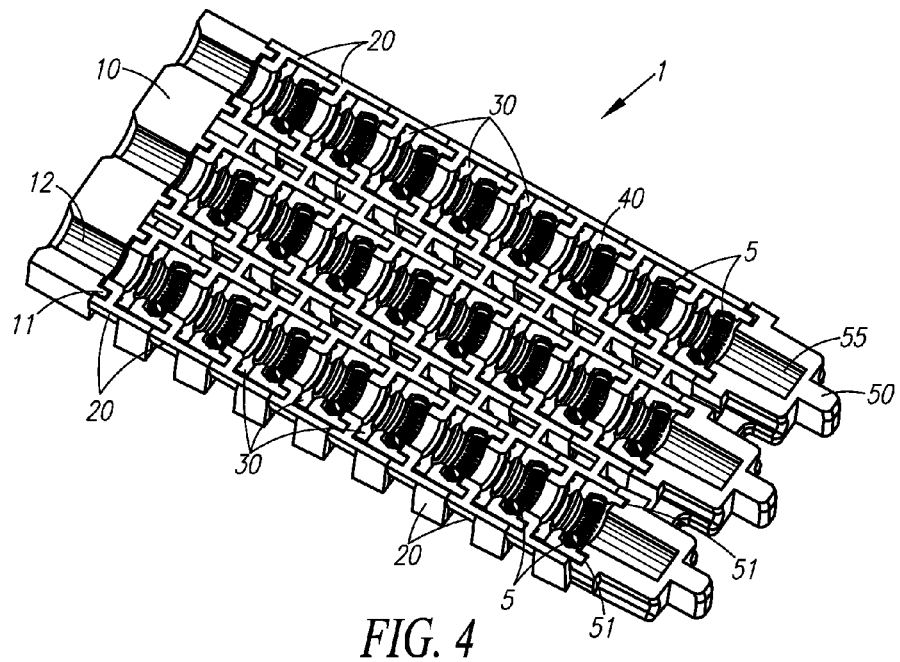
FIG. 4 shows a cross section of the example contact assembly of FIG. 3 flipped over.

FIG. 3 shows an example schematic of an example contact assembly that can be used with the lead frame discussed above. FIG. 4 shows a flipped cross section of the assembly of FIG. 3. The example contact assembly is comprised of a setscrew block 10 and an end cap 50 covering opposite ends of the contact assembly. A plurality of thermoplastic stacker components 20 are shown provided between the setscrew block 10 and the end cap 50. For the example embodiment, there is one stacker component per "row". Each of the thermoplastic stacker components is associated with a set of conductive contact blocks 40 (three per row are shown in the example embodiment, representing three "columns"), a set of corresponding seals 30 (3 per row in the example), and a set of contacts, such as springs 5 (again, 3 per row in the example). For this example embodiment shown in the figures, there are eight sets of stacker components (i.e., forming 8 "rows") with each stacker component (and thus each row) associated with a set of three contact block/seal/spring groupings (i.e., three "columns"). Of course, alternative embodiments could utilize alternative numbers of contact blocks (i.e., different numbers of rows), and each contact block might be associated with a different number of contact block/seal/spring groupings (i.e., different numbers of columns), such as using a single grouping, or two, four, five, or more groupings, depending on the desired implementation. Alternatively, the stacker components could be comprised of separate sub-components each associated with one of the contact blocks (hence for the example, there would be three sub-components).

The stacker component 20 has, for example, three open central portions including holes (bores), for receiving corresponding electrode pins 200 as described below (see FIG. 6). For any given stacker component, each open central portion is adapted for receiving a corresponding seal 30. Each seal 30 has a hole 33 formed in its center that is aligned with an associated hole of the stacker component for receiving the corresponding electrode pin 200.

Each stacker component is adapted to receive, on one side, either a part of a contact block 40 or a part of a setscrew block 10, while another side is adapted to receive a part of another contact block 40 between two block tabs 23 of the stacker component 20.

Each contact block 40 has a conductive contact surface 43 on contact tab 44 that, when paired with the second side of an associated stacker component 40, is exposed between the associated pair of block tabs 23 of the stacker component, the conductive contact surface 43 being exposed for electrically connecting to a contact lead 102 (see FIG. 7). Each contact block 40 also has an interior hole and a hollowed out interior portion with a groove for holding a corresponding spring 5. Each spring 5 is formed in a ring (donut) shape of conductive material with a void in its center (for receiving the associated electrode pin 200) and is in electrical contact with its corresponding contact block to ensure electrically conductivity.

Figure 6:
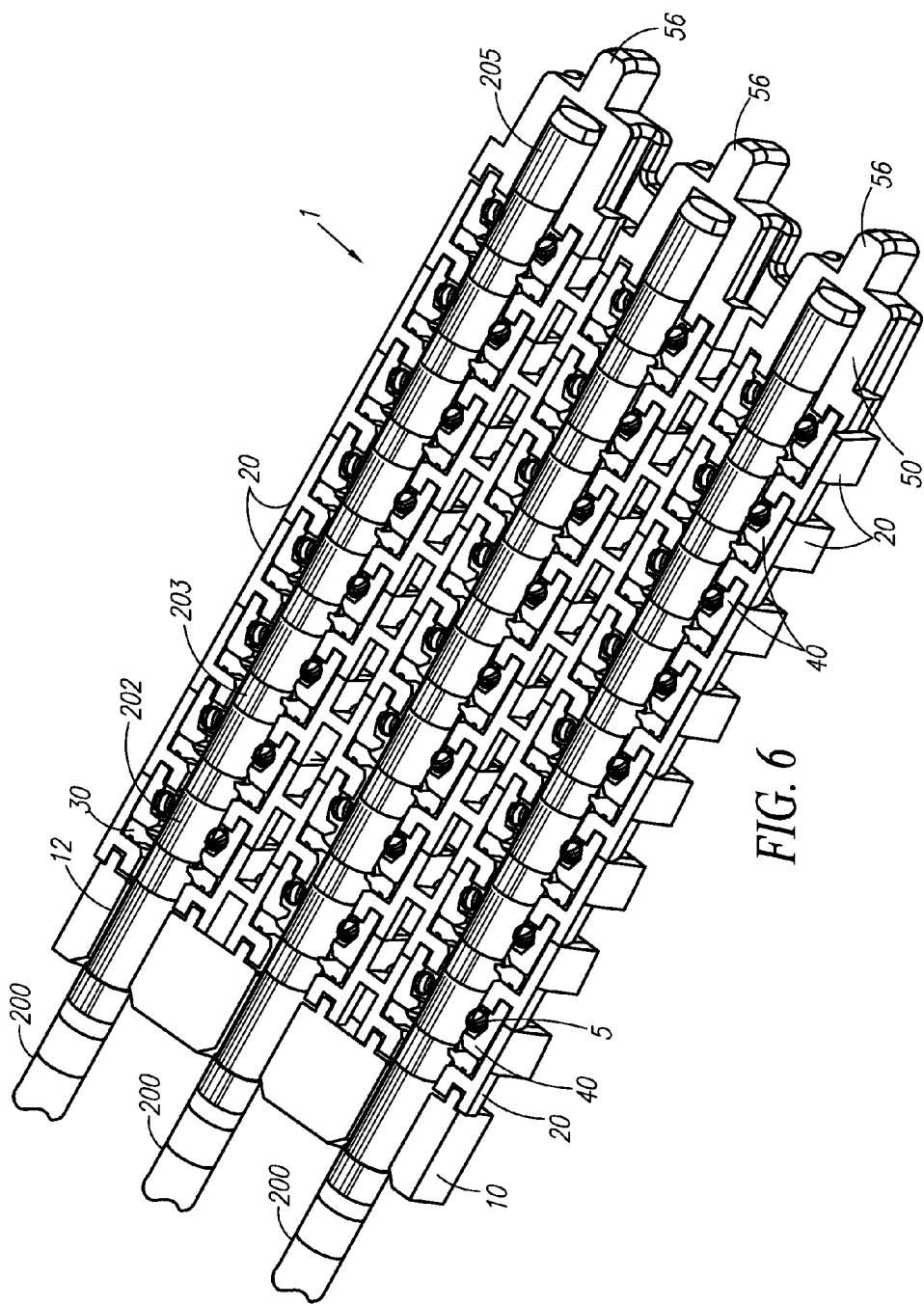
FIG. 6 shows the cross section of the contact assembly of FIG. 4 with example electrode pins installed therein.

The springs 5 are, in the example embodiment, torsion springs formed into a ring (a toroid/"donut" shape) having a space or hole in the center for receiving the corresponding electrode pin 200 (see FIG. 6). When the electrode pins 200 are inserted therethrough, the springs flex (cant) against and in electrical contact with a corresponding conductive surface portion, such as conductive ring 202 on the surface of the electrode pin 200 to make electrical contact with the conductive ring 202, as illustrated in FIG. 6. Alternative means of providing electrical contact between the electrode pin conductive rings 202 and the contact blocks could also be provided, such as by using metal tabs or different spring mechanisms, if desired, or integrating a contact structure directly in the contact block itself.

In most situations, each contact block is received by (mates with) a first side of a following stacker component 20 which acts to "cap" the components of a previous row assembled in the stacker component 20 and help hold them in place. The contact tab 44 fits between the block tabs 23, with the block tabs 23 extending beyond corresponding ends of the contact tab 44 and exposing a flat outer contact surface 43. If the contact block 40 is part of the last row of the device 1, the second cylindrical portion 42 is instead received by (mates with) the end cap 50.

Hence, for the example embodiment, each stacker component 20 is associated with a plurality (three each in the example embodiment) of seals 30, three contact blocks 40, and three springs 5, to create a row (layer).

FIG. 5 shows the contact assembly of the example embodiment connected to three sets (groups) of lead frames 100, each having 8 leads 101, with each lead 101 having an end 102 adapted for being attached to the exposed outer contact surface 43 of a corresponding contact tab 44 (see, e.g., FIGS. 3-4) and having a weld point 103. The leads 101 are conveniently routed in an organized manner around the tabs and other components of the stacker components to avoid shorting any of the leads together, such that each of the lead frames have leads that are routed differently from each other (as shown by the examples of FIGS. 1-2, versus the differently routed lead fames shown in FIGS. 10 and 11). Each of the leads 101 has a connector 105 at the other one end for connecting to a corresponding electrical connection point 160 on the IPG (as shown in FIG. 7). Thus, a conductive path is provided from one point 160 on the IPG, to the lead connector 105 connected to the point 160, down the associated lead 101 to the other end 102 to the corresponding contact block 40 to which the end 102 is connected, through the contact block to the associated spring 5 inserted therein, and on to the corresponding conductive ring 202, in contact with the spring 5, of the electrode pin 200 inserted through that contact block 40, and ultimately to an electrode, such as might be implanted near the spine of a patient for providing pulse therapy.

As shown in example of FIG. 6, three bores (columns) are defined through each of the eight rows of example contact assembly 1, with each of the bores/columns for receiving the corresponding one of the electrode pins 200 (thereby supporting three pins of eight conductors each). The pins are comprised of conductive rings 202 (each corresponding to one of the conductors of the electrode pin) and insulating portions 203. Because each pin supports a plurality of conductors, each pin can support a like plurality of electrodes for the desired medical therapy. Each of the bores is defined by the appropriate axial alignment of one of the holes 12 provided through the setscrew block 10, the hole (33) of one of the seals (30) in each row (inserted in its corresponding contact holder 25), and the hole (center) of one of the springs 5 (that are inserted in their corresponding of the contact block 40) in each row, and finally to one of the bores 55 of the end cap 50, in a manner sufficient to ensure that the electrode pins are adequately held in place and provide the appropriate electrical contacts to the associated contact blocks.

The setscrew block 10 is preferably comprised of titanium, although it could be comprised of any strong biocompatible metal such as stainless steel, nickel alloys, etc. The block can be manufactured using a machining process, or a metal injection molding (MIM) process, for example. The setscrew block holds setscrews (not shown) that tighten on the electrode pins 200 setscrew rings and prevent the leads from moving out of alignment with the contacts and seals of the contact assembly. The setscrew block 10 has a set of three screws (not shown) that are used to set (fix) the electrode pins 200 in place, once inserted, although other means of fixing the pins in place could be utilized, or the electrode pins may be kept in place solely by friction contact with the seals and springs through which they pass, or by some other mechanism.

Each of the stacker components 20 is preferably comprised of a polymer such as Polysulfone, but it could be any biocompatible polymer or other composition of similar capability. The components 20 can be manufactured by using Injection molding, or a machining process suitable for its composition and size. The stacker components 20 hold the seals 30 and contact blocks 40 in alignment (axially and radially), control seal compression, and act as a precision spacer to maintain contact to contact pitch. In the example embodiment, the stack pitch is about 0.100" nominal and accepts an electrode pin of about 0.055" nominal diameter. This concept will work down to around 0.080" pitch and pretty much any diameter (limited by how small the toroidal springs can be wound). The tolerance in the stacker contributes to the overall stack tolerance, likewise each of the seals is can be compressed as a separate assembly, so compression is controlled by the tolerances in one contact block and one seal not by the stack in its entirety.

Each of the seals 30 is preferably comprised of an elastic material such as silicone, or another elastomeric biocompatible polymer, and can be manufactured by molding, for example. Alternatively, the seals could be molded directly onto the stackers so they would form a single piece. The seals align with nonconductive segments 203 between the contact points on the electrode pin 200 and conform to the electrode pin surface so that even if flooded with conductive liquid in the lead bore, adjacent contacts have a sufficiently high enough impedance (i.e. 50 k Ohms) between them that they cannot effectively communicate electrically.

Each of the contact blocks 40 is preferably comprised of an MP35N alloy (a commercially available nonmagnetic, nickel-cobalt-chromium-molybdenum alloy that has a unique combination of properties), although any conductive biocompatible metal or alloy could be used. The contact blocks 40 can be manufactured by using a metal injection molding (MIM) process, or machined using known machining methods. The contact blocks are used to make electrical contact with the springs 5, transfer electrical signals from the electrode pins 200 to the leads 101, form a weld surface for the leads 101, and compress the seals 30 (in conjunction with the stackers components 20).

The springs 5 are comprised of a small diameter (e.g., 0.0035" or less) coiled Pt—Ir wire joined into a continuous toroidal shaped helix. The assembly can be made compatible with, and thus utilize, springs such as those disclosed in U.S. Pat. Nos. 6,749,358 and 7,070,455, and U.S. Pat. App. Pub. No. 2008/0246231, incorporated herein by reference.

The end cap 50 is preferably comprised of the same or similar material discussed for the stacker components 20. Alternatively, the end cap 50 could be comprised of a biocompatible metal with the inclusion of additional seals to ensuring sealing, in particular where a conductive end cap might be desirable. The end cap forms the end of the pin bores and the depth of the holes 55 providing in the end caps (for receiving the end 205 of the electrode pins 200) registers the location where the electrode pins align with the rest of the stack.

The contact assembly 1 can be assembled on assembly pins, such as the electrode pins 200 or by using other pins of the appropriate size for aid in arranging the assembly components. For the example embodiment shown in the figures, one electrode pin is used through each one of the three bores. The pins help to maintain alignment in the stack and make the components and the stack easier to handle. For the example embodiment, the assembly is accomplished manually by hand, but could be automated where mass production is contemplated to cover the cost of the machine and robotics.

The assembled contact assembly with pins therein is placed into a shell or housing 180. The shell has a feature (including the slots 254 of FIG. 7) that interlocks with the end cap tabs 56 on one side, including a vertical wall that forms a hard stop for the end cap 50. The other side of the shell 180 has an elastomeric piece 170 through which the bores continue through the cylinders 250. The assembly pins are inserted through the cylinders 250 of the elastomeric piece 170 first, then the curved and angled surfaces of the shell 180 and end cap 50 allow the rest of the stack to be pushed into place. Now the connector stack is trapped in alignment between the hard stop at the end cap 50 and the elastomeric piece 170 which serves as a spring to hold the stack in compression. The assembly pins can then be removed. The shell can then be attached to the IPG (or possibly was pre-attached). Then the lead frames 100 are attached to the IPG and the contact blocks, with the leads 101 being welded or soldered to the contact tab 43 at weld/solder point 103 (see FIG. 5). Then the shell is filled with a potting material 252, such as silicone, for example. The potting material 252 surrounds the contact assembly and each of the leads and the IPG connection points to insulate the contact assembly electrically and physically hold the components in alignment to one another and binds the assembly together.

Figure 10:
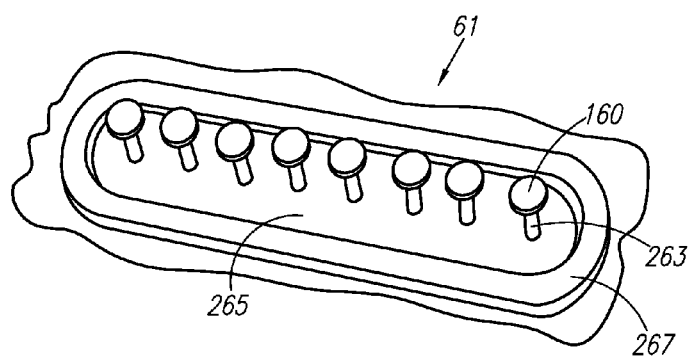
FIG. 10 shows an example arrangement of IPG pins on the example IPG.

FIG. 10 provides a block diagram of an example system including an IPG 61 that could utilize the contact assembly 1. The IPG 61 can be comprised of an internal power supply 301 (that may include a rechargeable battery), a controller 302, pulse generation electronics 303, protection/conditioning circuits 304, and the contact assembly 1 for connecting to an electrode array 180. The IPG 61 can be supported by an external power supply 310 (such as for charging the battery of the internal power supply 301), and a clinician programmer 330 and a user controller 320.

FIG. 11 shows an example application of the stimulator system for providing spinal stimulation. In that figure, the IPG 61 is shown implanted in a patient. Also shown is the human spine comprising the C1-C7 cervical vertebrae 65, the T1-T12 thoracic vertebrae 66, the L1-L5 lumbar vertebrae 67, and the S1-S6 sacral vertebrae 68. Electrodes 63 are shown disposed at the distal end of the spine and are positioned near the thoracic vertebrae 66. The Electrodes 63 are attached to the IPG 61 via electrode leads 64.

The leads and electrodes may be positioned anywhere along the spine to deliver the intended therapeutic effects of spinal cord electrical stimulation in the desired region of the spine. The distal end of the lead with its accompanying electrodes may be located along the epidural space and adjacent a desired portion of the spinal cord using well-established and known techniques for implanting and positioning SCS leads and electrodes, and the IPG 61 may be programmed using a clinician or other type of programmer 62 (such as a patient controller), as desired (and further described above). The electrode leads 64 can be connected to the IPG via a contact assembly as described in this application.

Many other example embodiments of the invention can be provided through various combinations of the above described features. Although the invention has been described hereinabove using specific examples and embodiments, it will be understood by those skilled in the art that various alternatives may be used and equivalents may be substituted for elements and/or steps described herein, without necessarily deviating from the intended scope of the invention. Modifications may be necessary to adapt the invention to a particular situation or to particular needs without departing from the intended scope of the invention. It is intended that the invention not be limited to the particular implementations and embodiments described herein, but that the claims be given their broadest reasonable interpretation to cover all novel and non-obvious embodiments, literal or equivalent, disclosed or not, covered thereby.

What is claimed is:

1. A connector assembly for installing in an implantable medical device including electronics connected to a plurality of conductive pins, said connector assembly connecting the conductive pins to an external interface, said connector assembly comprising a plurality of conductive leads, each one of said conductive leads including:
   an interface end connector configured for electrically connecting to a corresponding channel of the interface;
   a device end connector configured for electrically connecting to the medical device, said device end connector including a curved portion forming a slot configured to receive a corresponding one of the conductive pins of the medical device within the slot of said curved portion; and
   a conductive wire portion electrically connecting said interface end connector to said device end connector.

2. The connector assembly of claim 1, further comprising a first removable installation part connected to a plurality of said conductive leads such that the first removable installation part is connected to each device end connector by a corresponding one of a plurality of first breakable connections, wherein said first removable installation part is configured to be removed during installation of said connector assembly by breaking said plurality of first breakable connections.

3. The connector assembly of claim 2, further comprising a second removable installation part connected to a plurality of said conductive leads such that the second removable installation part is connected to each device end connector by a corresponding one of a plurality of second breakable connections, wherein said second removable installation part is configured to be removed during installation of said connector assembly by breaking said plurality of second breakable connections.

4. The connector assembly of claim 1, further comprising a second removable installation part connected to a plurality of said conductive leads such that the second removable installation part is connected to each device end connector by a corresponding one of a plurality of second breakable connections, wherein said second removable installation part is configured to be removed during installation of said connector assembly by breaking said plurality of second breakable connections.

5. The connector assembly of claim 1, wherein each said device end connector further includes:
   a flat terminal portion configured to contact a head portion of the corresponding conductive pin, and
   a flat base portion provided between said curved portion and said conductive wire portion, said flat base portion being configured for being placed against a portion of the medical device, wherein
   said flat terminal portion, said flat base portion, and said curved portion are arranged such that, when said device end connector is installed on the corresponding conductive pin, said flat terminal portion is compressed against said head portion of the corresponding conductive pin.

6. The connector assembly of claim 1, wherein each said device end connector further includes a flat terminal portion configured to contact a head portion of the corresponding conductive pin.

7. The connector assembly of claim 1, wherein a plurality of the conductive wire portions of said connector assembly are differently routed around various structures of said implantable medical device by providing bends at one or more locations in different ones of the plurality of conductive wire portions.

8. The connector assembly of claim 1, wherein the conductive wire portion of each one of said conductive leads has at least one bend therein that is different than a bend at a corresponding location in the conductive wire portions of the others of the conductive leads.

9. The connector assembly of claim 1, wherein each one of the conductive wire portions of said conductive leads is differently routed around various structures of said implantable medical device than the conductive wire portions of other ones of the plurality of conductive leads.

10. The connector assembly of claim 1, wherein said interface end connector includes a flat portion having a hole configured for supporting a weld for welding said flat portion to a corresponding conductor on said interface.

11. A connector assembly for installing in an implantable medical device including electronics connected to a plurality of conductive pins, said connector assembly connecting the conductive pins to an electrode interface, said connector assembly comprising:
   a plurality of conductive leads, each one of said conductive leads including:
      an interface end connector provided at one end and configured for electrically connecting to a corresponding channel of the electrode interface;
      a device end connector provided at another end and configured for electrically connecting to a corresponding one of the conductive pins of the medical device, said device end connector including a terminal portion, a base portion, and a curved portion connecting said terminal portion to said base portion, wherein
      said curved portion forms a slot configured to receive a first portion of the corresponding conductive pin of the medical device, wherein said terminal portion is configured to receive a second portion of the corresponding conductive pin, and wherein said base portion is configured to be placed against a portion of the implantable medical device; and
      a conductive wire portion connecting said interface end connector to said device end connector.

12. The connector assembly of claim 11, further comprising a first installation part connected to a plurality of said conductive leads configured for holding said plurality of conductive leads together for installation into the medical device.

13. The connector assembly of claim 12, wherein said first installation part is configured to be removed from said connector assembly when said connector assembly is installed in the implantable medical device.

14. The connector assembly of claim 11, further comprising a first removable installation part connected to a plurality of said conductive leads such that the first removable installation part is connected to each device end connector by a corresponding one of a plurality of first breakable connections, wherein said first removable installation part is configured to be removed during installation of said connector assembly by breaking said plurality of first breakable connections.

15. The connector assembly of claim 11, further comprising a second removable installation part connected to a plurality of said conductive leads such that the second removable installation part is connected to each interface end connector by a corresponding one of a plurality of second breakable connections, wherein said second removable installation part is configured to be removed during installation of said connector assembly by breaking said plurality of second breakable connections.

16. The connector assembly of claim 11, wherein a plurality of the conductive wire portions of said connector assembly are differently routed around various structures of said implantable medical device by providing bends at one or more locations in different ones of the plurality of conductive wire portions.

17. The connector assembly of claim 11, wherein said interface end connector includes a flat portion having a hole for supporting a weld for welding said flat portion to a corresponding one of a plurality of conductors provided on said electrode interface.

18. A connector assembly for installing in an implantable medical device including electronics connected to a plurality of conductive pins, said connector assembly connecting the conductive pins to an electrode interface, said connector assembly comprising:
  a plurality of conductive leads, each one of said conductive leads including:
    an interface end connector provided at one end and configured for electrically connecting to a corresponding channel of the electrode interface,
    a device end connector provided at another end and configured for electrically connecting to a corresponding one of said conductive pins of the medical device, said device end connector including a flat terminal portion, a flat base portion, and a curved portion connecting said flat terminal portion to said flat base portion, wherein
    said curved portion forms a slot configured to receive a first portion of the corresponding conductive pin of the medical device, said flat terminal portion is configured to receive a second portion of the corresponding conductive pin, and wherein said flat base portion is configured to be placed against a portion of the implantable medical device, and
    a conductive wire portion connecting said interface end connector to said device end connector.

19. The connector assembly of claim 18, wherein said flat terminal portion, said flat base portion, and said curved portion of said device end connector are configured to be under compression when installed on said corresponding pin of said medical device.

20. A connector assembly for installing in an implantable medical device including electronics connected to a plurality of conductive pins, said connector assembly for connecting the conductive pins to an electrode interface, said connector assembly comprising:
  a plurality of conductive leads, each one of said conductive leads including:
    an interface end connector provided at one end and configured for electrically connecting to a corresponding channel of the electrode interface,
    a device end connector provided at another end and configured for electrically connecting to a corresponding one of said conductive pins of the medical device, said device end connector including a flat terminal portion, a flat base portion, and a curved portion connecting said flat terminal portion to said flat base portion, wherein
    said curved portion forms a slot configured to receive a first portion of a corresponding one of the conductive pins of the medical device, said flat terminal portion is configured to receive a second portion of the corresponding one of the conductive pins and wherein said flat base portion is configured to be placed against a portion of the implantable medical device, and
    a conductive wire portion connecting said interface end connector to said device end connector;
  a first installation part connected to each device end connector of said plurality of conductive leads; and
  a second installation part connected to each interface end connector of said a plurality of said conductive leads, wherein
  said first installation part and said second installation part are configured to be removed during installation of said connector assembly in said implantable medical device.

21. The connector assembly of claim 20, wherein said interface end connector includes a flat portion having a hole for supporting a weld for welding said flat portion to a corresponding conductor on said electrode interface.

22. A connector assembly for installing in an implantable medical device including electronics connected to a plurality of conductive pins, said connector assembly connecting the conductive pins to an electrode interface, said connector assembly comprising:
  a plurality of conductive leads, each one of said conductive leads including:
    an interface end connector provided at one end and having a flat portion configured for electrically connecting to one of a plurality of conductors of the electrode interface,
    a device end connector provided at another end and configured for electrically connecting to a corresponding one of said conductive pins of the medical device, said device end connector including a flat terminal portion, a flat base portion, and a curved portion connecting said flat terminal portion to said flat base portion, wherein
    said curved portion forms a slot configured to receive a first portion of the corresponding conductive pin of the medical device, said flat terminal portion is configured to receive a second portion of the corresponding pin, and wherein said flat base portion is configured to be placed against a portion of the implantable medical device, such that said device end connector provided under compression when said device end connector is installed on the corresponding pin, and
    a conductive wire portion connecting said interface end connector to said device end connector.

23. The connector assembly of claim 22, further comprising at least one installation part connected to said connector assembly, said installation part being configured to be removed during installation of said connector assembly in said implantable medical device.

24. A connector assembly for installing in an implantable medical device including electronics connected to a plurality of conductive pins, said connector assembly connecting the conductive pins to an electrode interface, said connector assembly comprising:
  a plurality of conductive leads, each one of said conductive leads including:
    an interface end connector provided at one end and configured for electrically connecting to a corresponding channel of the electrode interface,
    a device end connector provided at another end and configured for electrically connecting to a corresponding one of the conductive pins of the medical device, said device end connector including a flat terminal portion, a flat base portion, and a curved portion connecting said flat terminal portion to said flat base portion, wherein said curved portion forms a slot configured to receive a first portion of the corresponding conductive pin of the medical device, said flat terminal portion is configured to receive a second portion of the corresponding conductive pin, and wherein said flat base portion is configured to be placed against a portion of the implantable medical device, and a conductive wire portion connecting said interface end connector to said device end connector;

a first removable installation part connected to a plurality of said conductive leads by connecting the first removable installation part to each device end connector via a corresponding one of a plurality of first breakable connections; and a second removable installation part connected to a plurality of said conductive leads by connecting the second removable installation part to each interface end connector via a corresponding one of a plurality of second breakable connections.

25. The connector assembly of claim 24, wherein said first removable installation part is configured to be removed during installation of said connector assembly by breaking said plurality of first breakable connections, and wherein said second removable installation part is configured to be removed during said installation of said connector assembly by breaking said second breakable connections.

26. The connector assembly of claim 24, wherein said interface end connector includes a flat portion having a hole for supporting a weld for welding said flat portion to a corresponding conductor on said interface.

27. A medical device for stimulating one or more stimulation regions of a patient, said medical device comprising:

an electrode interface having a plurality of electrical contacts, each one of said electrical contacts for carrying one of a plurality of channels and being configured for connecting to one of a plurality of electrodes, each one of said electrodes for stimulating one or more of said stimulation regions;

an electronic circuit for providing one or more therapy signals for each one of said plurality of channels;

a plurality of conductive pins installed on said medical device, each one of said conductive pins for connecting to said stimulation electronics for conducting one of said plurality channels, each conductive pin having a head portion and a body portion; and a plurality of conductive leads, each one of said conductive leads including:

an interface end connector configured for electrically connecting to a corresponding one of said electrical contacts provided in the electrode interface, a device end connector for connecting to a corresponding one of the conductive pins, said device end connector including a flat terminal portion, a flat base portion, and a curved portion connecting said flat terminal portion to said flat base portion, wherein said curved portion forms a slot configured to receive the body portion of the corresponding conductive pin, wherein said flat terminal portion is configured to receive the head portion of the corresponding conductive pin, and wherein said flat base portion is configured to be placed against a portion of the medical device such that said device end connector is under compression when installed on the corresponding conductive pin, and a conductive wire portion connecting said interface end connector to said device end connector, wherein for a plurality of the conductive leads, the conductive wire portions are configured to be routed through said medical device by one or more bends provided in the conductive wire portions.

28. The medical device of claim 27, wherein said flat terminal portion of the conductive leads are welded to the head portion of the corresponding conductive pin.

29. The medical device of claim 27, wherein said connector assembly further comprises a removable installation part having a plurality of breakable connections each connected to one of a plurality of the interface end connectors or each connected to one of a plurality of the device end connectors, wherein said removable installation part is configured to be removed during installation of said connector assembly by breaking said plurality of breakable connections.

* * * * *